(12) United States Patent
Kim et al.

(10) Patent No.: US 11,081,729 B2
(45) Date of Patent: Aug. 3, 2021

(54) NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME

(71) Applicant: LG Chem, Ltd., Seoul (KR)

(72) Inventors: Hyun Seung Kim, Daejeon (KR); Sung Hoon Yu, Daejeon (KR); Jeong Woo Oh, Daejeon (KR); Chul Haeng Lee, Daejeon (KR)

(73) Assignee: LG Chem, Ltd.

( * ) Notice: Subject to any disclaimer, the term of this patent is extended or adjusted under 35 U.S.C. 154(b) by 213 days.

(21) Appl. No.: 16/340,269

(22) PCT Filed: Jul. 6, 2018

(86) PCT No.: PCT/KR2018/007729
§ 371 (c)(1),
(2) Date: Apr. 8, 2019

(87) PCT Pub. No.: WO2019/013501
PCT Pub. Date: Jan. 17, 2019

(65) Prior Publication Data
US 2020/0044287 A1 Feb. 6, 2020

(30) Foreign Application Priority Data

Jul. 14, 2017 (KR) .................. 10-2017-0089773
Jul. 4, 2018 (KR) .................. 10-2018-0077576

(51) Int. Cl.
*H01M 10/0567* (2010.01)
*C07C 229/30* (2006.01)
(Continued)

(52) U.S. Cl.
CPC ....... *H01M 10/0567* (2013.01); *C07C 229/30* (2013.01); *C07D 207/16* (2013.01);
(Continued)

(58) Field of Classification Search
None
See application file for complete search history.

(56) References Cited

U.S. PATENT DOCUMENTS 6,159,640 A 12/2000 Appel et al.
2002/0115881 A1* 8/2002 Holzl .................. C07C 229/30
558/441

(Continued)

FOREIGN PATENT DOCUMENTS

CN 103078139 A 5/2013
DE 19724709 A1 12/1998
(Continued)

OTHER PUBLICATIONS

International Search Report for PCT/KR2018/007729, dated Oct. 8, 2018.
(Continued)

*Primary Examiner* — Wyatt P McConnell
(74) *Attorney, Agent, or Firm* — Lerner, David, Littenberg, Krumholz & Mentlik, LLP (57) ABSTRACT

The present invention relates to a non-aqueous electrolyte solution additive, and a non-aqueous electrolyte solution for a lithium-ion battery and a lithium-ion battery which include the same, and particularly, to a non-aqueous electrolyte solution, which may remove an acid generated by the decomposition of a lithium salt while being able to suppress the dissolution of metal impurities causing failure in the battery by using and including a Lewis base compound containing a propargyl group as a non-aqueous electrolyte solution additive for a lithium-ion battery, and a lithium (Continued)

secondary battery in which transition metal dissolution in a positive electrode and a low-voltage phenomenon are improved.

16 Claims, 2 Drawing Sheets

(51) Int. Cl.
| | |
|---|---|
| *C07D 207/16* | (2006.01) |
| *C07D 211/60* | (2006.01) |
| *C07D 233/90* | (2006.01) |
| *C07D 241/04* | (2006.01) |
| *C07D 295/145* | (2006.01) |
| *H01M 4/505* | (2010.01) |
| *H01M 4/525* | (2010.01) |
| *H01M 10/0525* | (2010.01) |
| *H01M 10/0568* | (2010.01) |
| *H01M 10/0569* | (2010.01) |
| *H01M 4/02* | (2006.01) |

(52) U.S. Cl.
CPC .......... *C07D 211/60* (2013.01); *C07D 233/90* (2013.01); *C07D 241/04* (2013.01); *C07D 295/145* (2013.01); *H01M 4/505* (2013.01); *H01M 4/525* (2013.01); *H01M 10/0525* (2013.01); *H01M 10/0568* (2013.01); *H01M 10/0569* (2013.01); *H01M 2004/028* (2013.01); *H01M 2300/0025* (2013.01)

(56) References Cited

U.S. PATENT DOCUMENTS

| | | | |
|---|---|---|---|
| 2011/0045361 A1 | 2/2011 | Abe et al. | |
| 2013/0216919 A1 | 8/2013 | Tokuda et al. | |
| 2013/0337317 A1 | 12/2013 | Shima et al. | |
| 2014/0308564 A1 | 10/2014 | Kim et al. | |
| 2018/0358655 A1* | 12/2018 | Kono | H01G 11/22 |

FOREIGN PATENT DOCUMENTS

| | | |
|---|---|---|
| EP | 0575191 A1 | 12/1993 |
| JP | 5545291 B2 | 7/2014 |
| JP | 5880124 B2 | 3/2016 |
| JP | 2016139567 A | 8/2016 |
| JP | 2016192381 A | 11/2016 |
| KR | 100628629 B1 | 9/2006 |
| KR | 20080047642 A | 5/2008 |
| KR | 20130108286 A | 10/2013 |
| KR | 101340027 B1 | 12/2013 |
| WO | 2009122908 A1 | 10/2009 |
| WO | 2015111612 A1 | 7/2015 |
| WO | 2016158986 A1 | 10/2016 |

OTHER PUBLICATIONS

Lee, H.H., et al., "Thermal Stability of the Solid Electrolyte Interface on Carbon Electrodes of Lithium Batteries", Journal of the Electrochemical Society, vol. 151, No. 4, Apr. 2004, pp. A542-A547.
Sloop, S., et al., "The Role of Li-Ion Battery Electrolyte Reactivity in Performance Decline and Self-Discharge", Journal of Power Sources, vol. 119, Jun. 2003, pp. 330-337.
Bhat, et al., "A mild and selective method for N-dealkylation of tertiary amines," Tetrahedron Letters, Sep. 21, 2004, pp. 7983-7985, vol. 45, No. 43.
De Geest, et al., "Biodegradable microcapsules designed via 'click' chemistry," Chemical Communications, Nov. 14, 2007, pp. 190-192, No. 2.
Extended European Search Report with written opinion for Application No. 18832898.3 dated Nov. 27, 2019, 12 pages.
Rehders, et al., "Synthesis of Dihydroxyethylene Isoteres of Dipeptides. 1. Enantiomerically and Diastereomerically Pure 2-Alkyl-5-amino-3-dimethylphenylsilyl-4-octanolides from (S)-N,N-Dibenzyl-leucinal," Synthesis, Jan. 1, 1992, pp. 859-864, vol. 1992, No. 09.
Wilkins, et al., "Pathways to Functionalized Heterocycles: Propargyl Rearrangement Using B(C6F5)3," Organometallics, Oct. 21, 2015, pp. 5298-5309, vol. 34, No. 21.
Wu, et al., "Efficiency and Fidelity in a Click-Chemistry Route to Triazole Dendrimers by the Copper (I)-Catalyzed Ligation of Azides and Alkynes," Angewandte Chemie, International Edition, Jun. 30, 2004, pp. 3928-3932, vol. 43.

* cited by examiner

NON-AQUEOUS ELECTROLYTE SOLUTION ADDITIVE, AND NON-AQUEOUS ELECTROLYTE SOLUTION FOR LITHIUM SECONDARY BATTERY AND LITHIUM SECONDARY BATTERY WHICH INCLUDE THE SAME

CROSS-REFERENCE TO RELATED APPLICATIONS

The present application is a national phase entry under 35 U.S.C. § 371 of International Application No. PCT/KR2018/007729 filed Jul. 6, 2018, which claims priority from Korean Patent Application No. 10-2018-0077576 filed Jul. 4, 2018 and Korean Patent Application No. 10-2017-0089773 filed Jul. 14, 2017, all of which are incorporated herein by reference.

TECHNICAL FIELD

The present invention relates to a non-aqueous electrolyte solution additive, and a non-aqueous electrolyte solution for a lithium secondary battery and a lithium secondary battery which include the same.

BACKGROUND ART

While personal IT devices and computer networks are developed due to the development of information society, and, as a result, the dependency of society as a whole on electrical energy has increased, there is a need to develop a technique for efficiently storing and utilizing the electrical energy.

A secondary battery-based technique is the most suitable technique for various applications, wherein, since miniaturization is possible, it may be applied to personal IT devices, and it may also be applied to large devices such as power storage devices.

Among the secondary battery techniques, a lithium-ion battery, as a battery system with theoretically the highest energy density, is in the spotlight.

With respect to the lithium-ion battery, unlike the early days when lithium metal was directly used in the system, it is composed of a positive electrode formed of a transition metal oxide containing lithium, a negative electrode capable of storing the lithium, an electrolyte solution, and a separator.

With respect to the positive electrode among these components, energy is stored through a redox reaction of transition metal, wherein this results in the fact that the transition metal must be essentially included in a positive electrode material.

In the preparation of the lithium-ion battery, low-voltage failure of the battery is currently pointed out as a major problem. With respect to the low-voltage failure, a potential of the battery gradually drops after an activation process to lose its value as a product, wherein such a phenomenon is caused by the following three causes.

First, it is observed when passivation ability of a film formed on surfaces of the positive electrode/negative electrode after the activation process is reduced.

With respect to particularly the negative electrode among electrode materials of the lithium-ion battery, a graphite-based negative electrode is used in most cases, wherein, with respect to graphite, since its operating potential is 0.3 V (vs. Li/Li$^+$) or less which is lower than an electrochemical stabilization window of the electrolyte solution used in the lithium-ion battery, the electrolyte solution is first reduced and decomposed. The electrolyte solution product thus reduced and decomposed forms a solid electrolyte interphase (SEI) that transmits lithium ions but suppresses further decomposition of the electrolyte solution.

However, in a case in which the SEI does not have sufficient passivation ability to suppress the further decomposition of the electrolyte solution, the electrolyte solution is further decomposed during storage so that the charged graphite is self-discharged, and, consequently, a phenomenon occurs in which the potential of the entire battery is reduced. This factor is also a major cause of the low-voltage failure.

Second, it occurs when metallic impurities are included during the preparation of an initial electrode slurry.

For example, the positive electrode of the lithium-ion battery is prepared by coating a slurry including a conductive agent and a binder as well as an electrode active material on a current collector such as aluminum, wherein, in this case, metal powder, such as iron, copper, or nickel powder, generated during the preparation of the conductive agent may not be removed but may be contained during the preparation of the electrode.

With respect to the metal impurities initially contained, there are many cases where a large amount of the metal impurities exists locally in the electrode, and, as a result, during the activation process before initial shipment of the battery, an excessive amount of metal ions is dissolved from the positive electrode and electrodeposited on the negative electrode to grow as dendrites. This eventually causes an internal short-circuit of the battery, and a low-voltage failure rate may be dramatically increased.

Third, it occurs when the transition metals are easily dissolved from the positive electrode in the electrolyte solution.

That is, the transition metals constituting the positive electrode may be easily dissolved in the electrolyte solution due to HF generated in the electrolyte solution or the formation of an unstable structure caused by charge and discharge of the positive electrode, wherein transition metal ions thus dissolved are again electrodeposited on the positive electrode to be a cause of increasing resistance of the positive electrode, or, in contrast, after being moved to the negative electrode through the electrolyte solution, the transition metal ions are electrodeposited on the negative electrode to self-discharge the negative electrode and destruct the SEI that gives passivation ability to the negative electrode, and, thus, it is known as a factor to consume lithium ions or increase interfacial resistance of the negative electrode while promoting an additional electrolyte solution decomposition reaction.

The dissolution of the transition metal and the insufficient passivation ability of the SEI become a cause of degradation due to the transition metal ion species dissolved from the positive electrode during high temperature charge/discharge or high temperature storage as well as the activation process step.

Thus, in a lithium-ion battery using positive electrode materials in which the dissolution of transition metal occurs, studies have been conducted to improve performance, such as high-temperature lifetime and storage, by introducing an additive capable of improving low-voltage failure.

PRIOR ART DOCUMENT

*J. Power Sources*, 119-121 (2003) 330-337
*J. Electrochem. SOC.*, 151 (2004) A542-A547

DISCLOSURE OF THE INVENTION

Technical Problem

An aspect of the present invention provides a non-aqueous electrolyte solution additive having an excellent adhesion effect to metal impurities as well as an excellent effect of removing a decomposition product generated from a lithium salt to improve a low-voltage phenomenon of a lithium-ion battery and dissolution of transition metal in a positive electrode.

Another aspect of the present invention provides a non-aqueous electrolyte solution for a lithium secondary battery which includes the non-aqueous electrolyte solution additive.

Another aspect of the present invention provides a lithium secondary battery which includes the non-aqueous electrolyte solution for a lithium secondary battery.

Technical Solution

According to an aspect of the present invention, there is provided a non-aqueous electrolyte solution additive which is at least one compound selected from the group consisting of compounds represented by Formulae 1 and 2.

(Formula 1)

In Formula 1,

R1 and R2 are each independently a linear or non-linear alkyl group having 1 to 5 carbon atoms, and $R_3$ is a linear or non-linear alkylene group having 1 to 3 carbon atoms.

(Formula 2)

In Formula 2, $R_4$ is a linear or non-linear alkylene group having 1 to 3 carbon atoms, A is a substituted or unsubstituted nitrogen-containing heteroaryl group having 3 to 6 carbon atoms, a substituted or unsubstituted nitrogen-containing heteroaryl group having 3 to 6 carbon atoms which includes at least one of oxygen and nitrogen elements, a substituted or unsubstituted nitrogen-containing heterocyclic group having 3 to 6 carbon atoms, or a substituted or unsubstituted nitrogen-containing heterocyclic group having 3 to 6 carbon atoms which includes at least one of oxygen and nitrogen elements, $R_5$ is at least one selected from the group consisting of hydrogen, an alkyl group having 1 to 3 carbon atoms, oxygen (=O), —CN, and

, wherein R is a linear or non-linear alkylene group having 1 to 3 carbon atoms, n is an integer of 1 to 6, and when n is 2 or more, $R_5$'s may be the same or different from each other.

The compound represented by Formula 1 may include at least one selected from the group consisting of compounds represented by Formulae 1a to 1c below.

(Formula 1a)

(Formula 1b)

(Formula 1c)

Also, the compound represented by Formula 2 may include at least one selected from the group consisting of compounds represented by Formulae 2a to 2c below.

[Formula 2a]

In Formula 2a, $R_6$ is a linear or non-linear alkylene group having 1 to 3 carbon atoms, $R_7$ to $R_{10}$ are each independently at least one selected from the group consisting of hydrogen, an alkyl group having 1 to 3 carbon atoms, and —CN, and

B is $CH_2$, O, N—$CH_3$, C=O, or

, wherein R' is a linear or non-linear alkylene group having 1 to 3 carbon atoms.

[Formula 2b]

In Formula 2b, $R_{11}$ is a linear or non-linear alkylene group having 1 to 3 carbon atoms, and $R_{12}$ to $R_{15}$ are each independently at least one selected from the group consisting of hydrogen, an alkyl group having 1 to 3 carbon atoms, and —CN.

[Formula 2c]

In Formula 2c, $R_{16}$ is a linear or non-linear alkylene group having 1 to 3 carbon atoms, and

$R_{17}$ to $R_{19}$ are each independently at least one selected from the group consisting of hydrogen, an alkyl group having 1 to 3 carbon atoms, and —CN, and D is CH, or N.

Specifically, the compound represented by Formula 2 may include at least one selected from the group consisting of compounds represented by Formulae 2b and 2c, and, for example, may include the compound represented by Formula 2c.

The compound represented by Formula 2a may include at least one selected from the group consisting of compounds represented by Formulae 2a-1 to 2a-7 below.

(Formula 2a-1)

(Formula 2a-2)

(Formula 2a-3)

(Formula 2a-4)

(Formula 2a-5)

(Formula 2a-6)

(Formula 2a-7)

Furthermore, the compound represented by Formula 2b may include a compound represented by Formula 2b-1.

(Formula 2b-1)

The compound represented by Formula 2c may include a compound represented by Formula 2c-1.

(Formula 2c-1)

According to another aspect of the present invention, there is provided a non-aqueous electrolyte solution for a lithium secondary battery including:

a lithium salt; an organic solvent; and a non-aqueous electrolyte solution additive, wherein the non-aqueous electrolyte solution additive includes at least one compound selected from the group consisting of the compounds represented by Formulae 1 and 2.

The non-aqueous electrolyte solution additive may be included in an amount of 0.05 wt % to 5 wt %, for example, 0.5 wt % to 3 wt % based on a total amount of the non-aqueous electrolyte solution.

According to another aspect of the present invention, there is provided a lithium secondary battery including a negative electrode, a positive electrode, a separator disposed between the negative electrode and the positive electrode, and a non-aqueous electrolyte solution, wherein the positive electrode includes at least one positive electrode active material selected from the group consisting of a lithium-nickel-manganese-cobalt-based oxide and a lithium-manganese-based oxide, and the non-aqueous electrolyte solution is the non-aqueous electrolyte solution for a lithium secondary battery of the present invention.

Specifically, the positive electrode active material may include a lithium-manganese-based oxide, and the lithium-manganese-based oxide may be $LiMn_2O_4$.

Advantageous Effects

In the present invention, since a Lewis base compound including a nitrogen element and a propargyl group is used as a non-aqueous electrolyte solution additive to improve a low-voltage phenomenon of a lithium-ion battery, a Lewis acid formed due to anion decomposition of a lithium salt may be removed and a more stable solid electrolyte interphase (SEI) may be formed on surfaces of a negative electrode and a positive electrode, and thus, dissolution of transition metal from the positive electrode due to a decomposition product of the lithium salt may be suppressed. Also, in the present invention, a lithium secondary battery, in which low-voltage failure is improved and the dissolution of the transition metal from the positive electrode is suppressed, may be prepared by using a non-aqueous electrolyte solution including the non-aqueous electrolyte solution additive.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

MODE FOR CARRYING OUT THE INVENTION

Hereinafter, the present invention will be described in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

In order to improve a low-voltage failure rate of a lithium-ion battery, it is important to suppress dissolution of impurities included in a positive electrode or design a film formed on a surface of an electrode, such as a negative electrode, to have excellent passivation ability. However, since it is difficult to fully address the dissolution of transition metal from the positive electrode in an electrolyte solution, degradation of the battery may be significantly suppressed if electrodeposition of metal ions on the negative electrode or positive electrode is fundamentally prevented by scavenging the dissolved metal ions in the electrolyte solution, and, thus, it is considered that a low-voltage improvement effect may also be obtained.

Therefore, in order to suppress and prevent initial failure of the battery which occurs due to the dissolution of the transition metal or loss of passivation ability of a positive electrode film or solid electrolyte interphase (SEI), the present invention aims at providing an additive which has an excellent metallic impurity adsorption effect and may enhance the passivation ability of the SEI on the surface of the negative electrode. With respect to the non-aqueous electrolyte solution additive of the present invention, since it contains a triple bond, it may not only strengthen the SEI as film of a negative electrode, but may also suppress the dissolution of metal by being adsorbed on a metal foreign matter. Particularly, with respect to the non-aqueous electrolyte solution additive of the present invention, since it has a functional group containing a nitrogen element which is a Lewis base functional group, it may remove a decomposition product, such as HF or $PF_5$, which is formed due to the decomposition of a lithium salt.

Also, the present invention aims at providing a non-aqueous electrolyte solution and a lithium secondary battery which may improve low-voltage failure by including the non-aqueous electrolyte solution additive.

Specifically, in an embodiment of the present invention, provided is a non-aqueous electrolyte solution additive which is at least one compound selected from the group consisting of compounds represented by Formulae 1 and 2 below.

(Formula 1)

In Formula 1,

R1 and R2 are each independently a linear or non-linear alkyl group having 1 to 5 carbon atoms, and $R_3$ is a linear or non-linear alkylene group having 1 to 3 carbon atoms.

(Formula 2)

In Formula 2, $R_4$ is a linear or non-linear alkylene group having 1 to 3 carbon atoms, A is a substituted or unsubstituted nitrogen-containing heteroaryl group having 3 to 6 carbon atoms, a substituted or unsubstituted nitrogen-containing heteroaryl group having 3 to 6 carbon atoms which includes at least one of oxygen and nitrogen elements, a substituted or unsubstituted nitrogen-containing heterocyclic group having 3 to 6 carbon atoms, or a substituted or unsubstituted nitrogen-containing heterocyclic group having 3 to 6 carbon atoms which includes at least one of oxygen and nitrogen elements, $R_5$ is at least one selected from the group consisting of hydrogen, an alkyl group having 1 to 3 carbon atoms, oxygen (=O), —CN, and wherein R is a linear or non-linear alkylene group having 1 to 3 carbon atoms, n is an integer of 1 to 6, and when n is 2 or more, $R_5$'s may be the same or different from each other.

Since the compounds represented by Formulae 1 and 2 contain a functional group functioning as a Lewis base including a nitrogen element in its structure, the compounds represented by Formulae 1 and 2 may not suppress decomposition of anions, such as $PF_6^-$, of the lithium salt, but may remove a Lewis acid, such as HF or $PF_5$, as the decomposition product formed due to the decomposition of the anions, from the electrolyte solution, and, thus, the compounds represented by Formulae 1 and 2 may suppress degradation behavior due to a chemical reaction of the positive electrode or negative electrode surface film caused by the Lewis acid. As a result, since an additional decomposition of the electrolyte solution of the battery due to destruction of the film may be prevented by suppressing the degradation of the film, self-discharge of the battery may finally be prevented.

Also, since the compounds represented by Formulae 1 and 2 have a propargyl functional group in the structure, the functional group may form an SEI with high passivation ability on the surface of the negative electrode while being reduced and decomposed, and, thus, high-temperature durability of the negative electrode itself may not only be improved, but an amount of transition metal electrodeposited on the negative electrode itself may be reduced. Further, the propargyl group may be adsorbed on surfaces of metallic impurities included in the positive electrode to make the dissolution of the impurities difficult, and, accordingly, an internal short-circuit, which may occur due to precipitation of the dissolved metal ions on the negative electrode may be suppressed. Furthermore, since the propargyl group may be easily reduced on the surface of the negative electrode, the propargyl group may form a stable film on the surface of the negative electrode, and thus, a self-discharge reaction of a graphite-based or silicon-based negative electrode due to an additional reduction decomposition reaction of the electrolyte solution caused by instability of the SEI may be prevented.

Through the comprehensive effects listed above, since the non-aqueous electrolyte solution additive including the compounds represented by Formulae 1 and 2 of the present invention may be adsorbed on the surface of metal to suppress the dissolution of the metal as ions, and thus, the non-aqueous electrolyte solution additive may not only suppress the occurrence of the internal short-circuit, but also may stably form the SEI and may prevent the destruction of the positive/negative electrode films due to the decomposition of the lithium salt. Therefore, the non-aqueous electrolyte solution additive may suppress the self-discharge reaction of the battery and, accordingly, may improve the low-voltage failure of the lithium-ion battery.

The compound represented by Formula 1 may include at least one selected from the group consisting of compounds represented by Formulae 1a to 1c below.

(Formula 1a)

(Formula 1b)

(Formula 1c)

Also, the compound represented by Formula 2 may include at least one selected from the group consisting of compounds represented by Formulae 2a to 2c below.

(Formula 2a)

In Formula 2a,

$R_6$ is a linear or non-linear alkylene group having 1 to 3 carbon atoms, $R_7$ to $R_{10}$ are each independently at least one selected from the group consisting of hydrogen, an alkyl group having 1 to 3 carbon atoms, and —CN, and B is $CH_2$, O, N—$CH_3$, C=O, or wherein R' is a linear or non-linear alkylene group having 1 to 3 carbon atoms.

(Formula 2b)

In Formula 2b, $R_{11}$ is a linear or non-linear alkylene group having 1 to 3 carbon atoms, and $R_{12}$ to $R_{15}$ are each independently at least one selected from the group consisting of hydrogen, an alkyl group having 1 to 3 carbon atoms, and —CN.

(Formula 2c)

In Formula 2c, $R_{16}$ is a linear or non-linear alkylene group having 1 to 3 carbon atoms, and $R_{17}$ to $R_{19}$ are each independently at least one selected from the group consisting of hydrogen, an alkyl group having 1 to 3 carbon atoms, and —CN, and

D is CH, or N.

In a case in which two or more carbonyl groups are substituted (included) in a cyclic group of the compound of Formula 2a, oxygen of the carbonyl groups may delocalize electrons of nitrogen by acting as a n-acceptor. Thus, with respect to the amide compound, an effect of the nitrogen atom as a Lewis base, that is, an effect of removing the Lewis acid may be reduced in comparison to an amine-based material.

Therefore, with respect to the non-aqueous electrolyte solution additive of the present invention, since the compound represented by Formulae 2b and 2c, particularly the compounds represented by Formula 2c in the compounds represented by Formula 2, may effectively remove the Lewis acid, as the decomposition product of the lithium salt, due to an imidazole functional group, as a Lewis base, in comparison to the compound represented by Formula 2a, the compound represented by Formula 2c may be more preferably used.

The compound represented by Formula 2a may include at least one selected from the group consisting of compounds represented by Formulae 2a-1 to 2a-7 below.

(Formula 2a-1)

(Formula 2a-2)

(Formula 2a-3)

(Formula 2a-4)

(Formula 2a-5)

(Formula 2a-6)

(Formula 2a-7)

Also, the compound represented by Formula 2b may include a compound represented by Formula 2b-1 below.

(Formula 2b-1)

Furthermore, the compound represented by Formula 2c may include a compound represented by Formula 2c-1 below.

(Formula 2c-1)

Also, in an embodiment of the present invention, provided is a non-aqueous electrolyte solution for a lithium secondary battery including:

a lithium salt;
an organic solvent; and
a non-aqueous electrolyte solution additive,
wherein the non-aqueous electrolyte solution additive is at least one compound of the compounds represented by Formulae 1 and 2.

In this case, the compounds represented by Formulae 1 and 2 may be included in an amount of 0.05 wt % to 5 wt %, particularly 0.5 wt % to 3 wt %, and more particularly 0.8 wt % to 1.2 wt % based on a total amount of the non-aqueous electrolyte solution.

In a case in which the amount of the compounds represented by Formulae 1 and 2 is included within the above range, a secondary battery having more improved overall performance may be prepared. For example, if the amount of the additive is in a range of 0.05 wt % to 5 wt %, an effect of stabilizing the SEI or an effect of suppressing the metal dissolution is excellent and an effect of controlling an increase in resistance of the film due to the decomposition of the additive is excellent.

In the non-aqueous electrolyte solution of the present invention, the lithium salt, which is included as an electrolyte, may be used without limitation so long as it is typically used in an electrolyte solution for a lithium secondary battery. For example, the lithium salt may include $Li^+$ as a cation, and may include any one selected from the group consisting of $F^-$, $Cl^-$, $Br^-$, $I^-$, $NO_3^-$, $N(CN)_2^-$, $BF_4^-$, $ClO_4^-$, $AlO_4^-$, $AlCl_4^-$, $PF_6^-$, $SbF_6^-$, $AsF_6^-$, $BF_2C_2O_4^-$, $BC_4O_8^-$, $(CF_3)_2PF_4^-$, $(CF_3)_3PF_3^-$, $(CF_3)_4PF_2^-$, $(CF_3)_5PF^-$, $(CF_3)_6P^-$, $CF_3SO_3^-$, $C_4F_9SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion.

Also, in the non-aqueous electrolyte solution according to the embodiment of the present invention, the organic solvent is not limited as long as it may minimize decomposition due to an oxidation reaction during charge and discharge of the battery and may exhibit desired characteristics with the additive. For example, an ether-based solvent, an ester-based solvent, or an amide-based solvent may be used alone or in mixture of two or more thereof.

As the ether-based solvent among the organic solvents, any one selected from the group consisting of dimethyl ether, diethyl ether, dipropyl ether, methylethyl ether, methylpropyl ether, and ethylpropyl ether, or a mixture of two or more thereof may be used, but the present invention is not limited thereto.

Furthermore, the ester-based solvent may include at least one compound selected from the group consisting of a cyclic carbonate compound, a linear carbonate compound, a linear ester compound, and a cyclic ester compound.

Among these compounds, specific examples of the cyclic carbonate compound may be any one selected from the group consisting of ethylene carbonate (EC), propylene carbonate (PC), 1,2-butylene carbonate, 2,3-butylene carbonate, 1,2-pentylene carbonate, 2,3-pentylene carbonate, vinylene carbonate, and fluoroethylene carbonate (FEC), or a mixture of two or more thereof.

Also, specific examples of the linear carbonate compound may be any one selected from the group consisting of dimethyl carbonate (DMC), diethyl carbonate (DEC), dipropyl carbonate, ethylmethyl carbonate (EMC), methylpropyl carbonate, and ethylpropyl carbonate, or a mixture of two or more thereof, but the present invention is not limited thereto.

Specific examples of the linear ester compound may be any one selected from the group consisting of methyl acetate, ethyl acetate, propyl acetate, methyl propionate, ethyl propionate, propyl propionate, and butyl propionate, or a mixture of two or more thereof, but the present invention is not limited thereto.

Specific examples of the cyclic ester compound may be any one selected from the group consisting of γ-butyrolactone, γ-valerolactone, γ-caprolactone, σ-valerolactone, and ε-caprolactone, or a mixture of two or more thereof, but the present invention is not limited thereto.

Among the ester-based solvents, since the cyclic carbonate-based compound well dissociates the lithium salt in the electrolyte due to high permittivity as a highly viscous organic solvent, the cyclic carbonate-based compound may be preferably used. Since an electrolyte solution having high electrical conductivity may be prepared when the above cyclic carbonate-based compound is mixed with the low viscosity, low permittivity linear carbonate-based compound, such as dimethyl carbonate and diethyl carbonate, and the linear ester-based compound in an appropriate ratio, the cyclic carbonate-based compound may be more preferably used.

The non-aqueous electrolyte solution of the present invention may further include an additive for forming an SEI, if necessary. As the additive for forming an SEI which may be used in the present invention, a silicon-based compound including a vinyl group, vinylene carbonate, vinyl ethylene carbonate, fluoroethylene carbonate, cyclic sulfite, saturated sultone, unsaturated sultone, and a non-cyclic sulfone may be used alone or in a mixture of two or more thereof.

In this case, the cyclic sulfite may include ethylene sulfite, methyl ethylene sulfite, ethyl ethylene sulfite, 4,5-dimethyl ethylene sulfite, 4,5-diethyl ethylene sulfite, propylene sulfite, 4,5-dimethyl propylene sulfite, 4,5-diethyl propylene sulfite, 4,6-dimethyl propylene sulfite, 4,6-diethyl propylene sulfite, and 1,3-butylene glycol sulfite, the saturated sultone may include 1,3-propane sultone and 1,4-butane sultone, the unsaturated sultone may include ethene sultone, 1,3-propene sultone, 1,4-butene sultone, and 1-methyl-1,3-propene sultone, and the non-cyclic sulfone may include divinyl sulfone, dimethyl sulfone, diethyl sulfone, methyl ethyl sulfone, and methyl vinyl sulfone.

Also, in an embodiment of the present invention,
provided is a lithium secondary battery including a positive electrode, a negative electrode, a separator disposed between the positive electrode and the negative electrode, and a non-aqueous electrolyte solution,
wherein the non-aqueous electrolyte solution for a lithium secondary battery of the present invention is included as the non-aqueous electrolyte solution.

Specifically, the lithium secondary battery of the present invention may be prepared by injecting the non-aqueous electrolyte solution of the present invention into an electrode assembly which is formed by sequentially stacking the positive electrode, the negative electrode, and the separator disposed between the positive electrode and the negative electrode. In this case, any positive electrode, negative electrode, and separator, which have typically been used in the preparation of a lithium secondary battery, may be used as the positive electrode, negative electrode, and separator which constitute the electrode assembly.

The positive electrode and the negative electrode constituting the lithium secondary battery of the present invention may be prepared by a conventional method and used.

First, the positive electrode may be prepared by forming a positive electrode material mixture layer on a positive electrode collector. The positive electrode material mixture layer may be formed by coating the positive electrode collector with a positive electrode slurry including a positive electrode active material, a binder, a conductive agent, and a solvent, and then drying and rolling the coated positive electrode collector.

The positive electrode collector is not particularly limited so long as it has high conductivity without causing adverse chemical changes in the battery, and, for example, stainless steel, aluminum, nickel, titanium, fired carbon, or aluminum or stainless steel that is surface-treated with one of carbon, nickel, titanium, silver, or the like may be used.

The positive electrode active material is a compound capable of reversibly intercalating and deintercalating lithium, wherein the positive electrode active material may include a lithium transition metal oxide including lithium and at least one metal selected from cobalt, manganese, nickel, or aluminum, and, specifically, the positive electrode active material may include a lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or lithium-manganese-based oxide having high capacity characteristics and stability of the battery, and, for example, may include a lithium-manganese-based oxide.

The lithium-nickel-manganese-cobalt-based oxide may include $Li(Ni_{1/3}Mn_{1/3}CO_{1/3})O_2$, $Li(Ni_{0.6}Mn_{0.2}Co_{0.2})O_2$, $Li(Ni_{0.5}Mn_{0.3}Co_{0.2})O_2$, $Li(Ni_{0.7}Mn_{0.15}CO_{0.15})O_2$, and $Li(Ni_{0.8}Mn_{0.1}CO_{0.1})O_2)$, and the lithium-manganese-based oxide may include $LiMn_2O_4$.

That is, with respect to the compound of the present invention, since it not only includes a Lewis base functional group capable of removing the Lewis acid as the decomposition product of the lithium salt, but also has a propargyl functional group capable of forming a film with high passivation ability on the negative electrode, a better effect of suppressing the metal dissolution may be achieved when, among the positive electrode active materials, the lithium-nickel-manganese-cobalt-based oxide and the lithium-manganese-based oxide, particularly, the lithium-manganese-based oxide with a high Mn content, in which a large amount of transition metal is dissolved and electrodeposited on the negative electrode to cause the degradation of the battery, is used.

In addition to the lithium-manganese-based oxide, the positive electrode active material of the present invention may further include at least one lithium transition metal oxide selected from the group consisting of lithium-cobalt-based oxide (e.g., $LiCoO_2$, etc.), lithium-nickel-based oxide (e.g., $LiNiO_2$, etc.), lithium-nickel-manganese-based oxide (e.g., $LiNi_{1-Y}Mn_YO_2$ (where $0<Y<1$), $LiMn_{2-Z}Ni_ZO_4$ (where $0<Z<2$), etc.), lithium-nickel-cobalt-based oxide (e.g., $LiNi_{1-Y1}Co_{Y1}O_2$ (where $0<Y1<1$), lithium-manganese-cobalt-based oxide (e.g., $LiCo_{1-Y2}Mn_{Y2}O_2$ (where $0<Y2<1$), $LiMn_{2-Z1}Co_{Z1}O_4$ (where $0<Z1<2$), etc.), lithium-nickel-manganese-cobalt-based oxide (e.g., $Li(Ni_pCo_qMn_{r1})O_2$ (where $0<p<1$, $0<q<1$, $0<r1<1$, and $p+q+r1=1$) or $Li(Ni_{p1}Co_{q1}Mn_{r2})O_4$ (where $0<p1<2$, $0<q1<2$, $0<r2<2$, and $p1+q1+r2=2$), etc.), and lithium-nickel-cobalt-transition metal (M) oxide (e.g., $Li(Ni_{p2}Co_{q2}Mn_{r3}M_{S2})O_2$ (where M is selected from the group consisting of aluminum (Al), iron (Fe), vanadium (V), chromium (Cr), titanium (Ti), tantalum (Ta), magnesium (Mg), and molybdenum (Mo), and p2, q2, r3, and s2 are atomic fractions of each independent elements, wherein $0<p2<1$, $0<q2<1$, $0<r3<1$, $0<S2<1$, and $p2+q2+r3+S2=1$)).

The positive electrode active material may be included in an amount of 80 wt % to 99 wt % based on a total weight of solid content in the positive electrode slurry.

The binder is a component that assists in the binding between the active material and the conductive agent and in the binding with the current collector, wherein the binder is commonly added in an amount of 1 wt % to 30 wt % based on the total weight of the solid content in the positive electrode slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene terpolymer (EPDM), a sulfonated EPDM, a styrene-butadiene rubber, a fluoro rubber, various copolymers, and the like.

The conductive agent is commonly added in an amount of 1 wt % to 30 wt % based on the total weight of the solid content in the positive electrode slurry.

Any conductive agent may be used as the conductive agent without particular limitation so long as it has conductivity without causing adverse chemical changes in the battery, and, for example, a conductive material, such as: carbon powder such as carbon black, acetylene black (or Denka black), Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include an organic solvent, such as N-methyl-2-pyrrolidone (NMP), and may be used in an amount such that desirable viscosity is obtained when the positive electrode active material as well as selectively the binder and the conductive agent are included. For example, the solvent may be included in an amount such that a concentration of the solid content in the slurry including the positive electrode active material as well as selectively the binder and the conductive agent is in a range of 50 wt % to 95 wt %, for example, 70 wt % to 90 wt %.

Also, the negative electrode may be prepared by forming a negative electrode material mixture layer on a negative electrode collector. The negative electrode material mixture layer may be formed by coating the negative electrode collector with a slurry including a negative electrode active material, a binder, a conductive agent, and a solvent, and then drying and rolling the coated negative electrode collector.

The negative electrode collector generally has a thickness of 3 μm to 500 μm. The negative electrode collector is not particularly limited so long as it has high conductivity without causing adverse chemical changes in the battery, and, for example, copper, stainless steel, aluminum, nickel, titanium, fired carbon, copper or stainless steel that is surface-treated with one of carbon, nickel, titanium, silver, or the like, an aluminum-cadmium alloy, or the like may be used. Also, similar to the positive electrode collector, the negative electrode collector may have fine surface roughness to improve bonding strength with the negative electrode active material. The negative electrode collector may be used in various shapes such as a film, a sheet, a foil, a net, a porous body, a foam body, a non-woven fabric body, and the like.

Furthermore, the negative electrode active material may include at least one selected from the group consisting of lithium metal, a carbon material capable of reversibly intercalating/deintercalating lithium ions, metals or alloys of lithium and these metals, a metal composite oxide, a material which may be doped and undoped with lithium, and a transition metal oxide.

As the carbon material capable of reversibly intercalating/deintercalating lithium ions, any carbon material may be used without particular limitation so long as it is a carbon-based negative electrode active material generally used in a lithium ion secondary battery, and, as a typical example, crystalline carbon, amorphous carbon, or both thereof may be used. Examples of the crystalline carbon may be graphite such as irregular, planar, flaky, spherical, or fibrous natural graphite or artificial graphite, and examples of the amorphous carbon may be soft carbon (low-temperature sintered carbon) or hard carbon, mesophase pitch carbide, and fired cokes.

As the metals or alloys of lithium and these metals, metals selected from the group consisting of copper (Cu), nickel (Ni), sodium (Na), potassium (K), rubidium (Rb), cesium (Cs), francium (Fr), beryllium (Be), magnesium (Mg), calcium (Ca), strontium (Sr), silicon (Si), antimony (Sb), lead (Pb), indium (In), zinc (Zn), barium (Ba), radium (Ra), germanium (Ge), aluminum (Al), and tin (Sn) or alloys of lithium and these metals may be used.

One selected from the group consisting of PbO, $PbO_2$, $Pb_2O_3$, $Pb_3O_4$, $Sb_2O_3$, $Sb_2O_4$, $Sb_2O_5$, GeO, $GeO_2$, $Bi_2O_3$, $Bi_2O_4$, $Bi_2O_5$, $Li_xFe_2O_3$ ($0 \leq x \leq 1$), $Li_xWO_2$ ($0 \leq x \leq 1$), and $Sn_xMe_{1-x}Me'_yO_z$ (Me: manganese (Mn), iron (Fe), Pb, or Ge; Me': Al, boron (B), phosphorus (P), Si, Groups I, II and III elements of the periodic table, or halogen; $0 < x \leq 1$; $1 \leq y \leq 3$; $1 \leq z \leq 8$) may be used as the metal composite oxide.

The material, which may be doped and undoped with lithium, may include Si, $SiO_x$ ($0 < x \leq 2$), a Si—Y alloy (where Y is an element selected from the group consisting of alkali metal, alkaline earth metal, a Group 13 element, a Group 14 element, transition metal, a rare earth element, and a combination thereof, and is not Si), Sn, $SnO_2$, and Sn—Y (where Y is an element selected from the group consisting of alkali metal, alkaline earth metal, a Group 13 element, a Group 14 element, transition metal, a rare earth element, and a combination thereof, and is not Sn), and a mixture of $SiO_2$ and at least one thereof may also be used. The element Y may be selected from the group consisting of Mg, Ca, Sr, Ba, Ra, scandium (Sc), yttrium (Y), Ti, zirconium (Zr), hafnium (Hf), Rf, V, niobium (Nb), Ta, dubidium (Db), Cr, Mo, tungsten (W), seaborgium (Sg), Tc (technetium), rhenium (Re), Bh (bohrium), Fe, Pb, ruthenium (Ru), osmium (Os), hassium (Hs), rhodium (Rh), iridium (Ir), palladium (Pd), platinum (Pt), Cu, silver (Ag), gold (Au), Zn, cadmium (Cd), B, Al, gallium (Ga), Sn, In, Ge, P, arsenic (As), Sb, bismuth (Bi), sulfur (S), selenium (Se), tellurium (Te), Po (polonium), and a combination thereof.

The transition metal oxide may include lithium-containing titanium composite oxide (LTO), vanadium oxide, and lithium vanadium oxide.

The negative electrode active material may be included in an amount of 80 wt % to 99 wt % based on a total weight of solid content in the negative electrode active material slurry.

The binder is a component that assists in the binding between the conductive agent, the active material, and the current collector, wherein the binder is commonly added in an amount of 1 wt % to 30 wt % based on the total weight of the solid content in the negative electrode active material slurry. Examples of the binder may be polyvinylidene fluoride (PVDF), polyvinyl alcohol, carboxymethylcellulose (CMC), starch, hydroxypropylcellulose, regenerated cellulose, polyvinylpyrrolidone, tetrafluoroethylene, polyethylene, polypropylene, an ethylene-propylene-diene polymer (EPDM), a sulfonated EPDM, a styrene-butadiene rubber, a fluoro rubber, and various copolymers thereof.

The conductive agent is a component for further improving the conductivity of the negative electrode active material, wherein the conductive agent may be added in an amount of 1 wt % to 20 wt % based on the total weight of the solid content in the negative electrode active material slurry. Any conductive agent may be used as the conductive agent without particular limitation so long as it has conductivity without causing adverse chemical changes in the battery, and, for example, a conductive material, such as: carbon powder such as carbon black, acetylene black, Ketjen black, channel black, furnace black, lamp black, or thermal black; graphite powder such as natural graphite with a well-developed crystal structure, artificial graphite, or graphite; conductive fibers such as carbon fibers or metal fibers; metal powder such as fluorocarbon powder, aluminum powder, and nickel powder; conductive whiskers such as zinc oxide whiskers and potassium titanate whiskers; conductive metal oxide such as titanium oxide; or polyphenylene derivatives, may be used.

The solvent may include water or an organic solvent, such as N-methyl-2-pyrrolidone (NMP) and alcohol, and may be used in an amount such that desirable viscosity is obtained when the negative electrode active material as well as selectively the binder and the conductive agent are included. For example, the solvent may be included in an amount such that a concentration of the solid content in the slurry including the negative electrode active material as well as selectively the binder and the conductive agent is in a range of 50 wt % to 95 wt %, for example, 70 wt % to 90 wt %.

Also, the separator plays a role in blocking an internal short-circuit between both electrodes and impregnating the electrolyte, wherein, after mixing a polymer resin, a filler, and a solvent to prepare a separator composition, the separator composition is directly coated on the electrode and dried to form a separator film, or, after the separator composition is cast on a support and dried, the separator may be prepared by laminating a separator film peeled from the support on the electrode.

A typically used porous polymer film, for example, a porous polymer film prepared from a polyolefin-based polymer, such as an ethylene homopolymer, a propylene homopolymer, an ethylene/butene copolymer, an ethylene/hexene copolymer, and an ethylene/methacrylate copolymer, may be used alone or in a lamination therewith as the separator. Also, a typical porous nonwoven fabric, for example, a nonwoven fabric formed of high melting point glass fibers or polyethylene terephthalate fibers may be used, but the present invention is not limited thereto.

In this case, the porous separator may generally have a pore diameter of 0.01 μm to 50 μm and a porosity of 5% to 95%. Also, the porous separator may generally have a thickness of 5 μm to 300 μm.

A shape of the lithium secondary battery of the present invention is not particularly limited, but a cylindrical type using a can, a prismatic type, a pouch type, or a coin type may be used.

Hereinafter, the present invention will be described in more detail according to examples. However, the invention may be embodied in many different forms and should not be construed as being limited to the embodiments set forth herein. Rather, these example embodiments are provided so that this description will be thorough and complete, and will fully convey the scope of the present invention to those skilled in the art.

EXAMPLES

Example 1

(Non-Aqueous Electrolyte Solution Preparation)

A non-aqueous electrolyte solution of the present invention was prepared by adding 0.05 g of the compound of Formula 2c-1 to 4.95 g of an organic solvent (ethylene carbonate:ethyl methyl carbonate=30:70 vol %) in which 1.0 M $LiPF_6$ was dissolved (see Table 1 below).

(Positive Electrode Preparation)

A 20 μm thick positive electrode collector (Al foil) was coated with a mixture, in which a ternary positive electrode active material ($Li(Ni_{0.8}Mn_{0.1}Co_{0.1})O_2$) containing nickel, cobalt, and manganese, as a positive electrode active material, carbon black as a conductive agent, and polyvinylidene fluoride (PVDF), as a binder, were mixed in a ratio of 97.5:1:1.5 (wt %), dried, and roll-pressed to prepare a positive electrode. A surface of the electrode thus prepared was coated with about 0.5 $mg/cm^2$ to about 0.6 $mg/cm^2$ of iron particles to prepare a positive electrode for a low-voltage failure simulation test.

(Secondary Battery Preparation)

The positive electrode including impurities, which was prepared by the above-described method, and lithium (Li) metal, as a negative electrode, were used to prepare a Li half-cell, and a porous polyethylene separator was then used to prepare a coin half-cell.

Example 2

A non-aqueous electrolyte solution and a coin half-cell including the same were respectively prepared in the same manner as in Example 1 except that 0.04 g of the compound of Formula 2c-1 was added to 4.96 g of the organic solvent during the preparation of the non-aqueous electrolyte solution.

Example 3

A non-aqueous electrolyte solution and a coin half-cell including the same were respectively prepared in the same manner as in Example 1 except that 0.06 g of the compound of Formula 2c-1 was added to 4.94 g of the organic solvent during the preparation of the non-aqueous electrolyte solution.

Comparative Example 1

A non-aqueous electrolyte solution and a coin half-cell including the same were prepared in the same manner as in Example 1 except that an additive was not included during the preparation of the non-aqueous electrolyte solution (see Table 1 below).

Comparative Example 2

A non-aqueous electrolyte solution and a coin half-cell including the same were prepared in the same manner as in Example 1 except that a compound of the following Formula 3 was included as a non-aqueous electrolyte solution additive during the preparation of the non-aqueous electrolyte solution (see Table 1 below).

[Formula 3]

Comparative Example 3

A non-aqueous electrolyte solution and a coin half-cell including the same were prepared in the same manner as in Example 1 except that a compound of the following Formula 4 was included as a non-aqueous electrolyte solution additive during the preparation of the non-aqueous electrolyte solution (see Table 1 below).

[Formula 4]

Comparative Example 4

A non-aqueous electrolyte solution and a coin half-cell including the same were prepared in the same manner as in Example 1 except that lithium oxalyldifluoroborate (Li-ODFB), a lithium salt-based compound, was included as a non-aqueous electrolyte solution additive during the preparation of the non-aqueous electrolyte solution (see Table 1 below).

Comparative Example 5

A non-aqueous electrolyte solution and a coin half-cell including the same were prepared in the same manner as in Example 1 except that succinonitrile (SN) was included as a non-aqueous electrolyte solution additive during the preparation of the non-aqueous electrolyte solution (see Table 1 below).

TABLE 1

| Examples | Lithium salt | Organic solvent Composition | Amount added (g) | Additive Formula | Amount added (g) | (wt %) |
|---|---|---|---|---|---|---|
| Example 1 | 1.0M | EC:EMC = 30:70 | 4.95 | 2c-1 | 0.05 | 1 |
| Example 2 | $LiPF_6$ | (vol %) | 4.96 | 2c-1 | 0.04 | 0.8 |
| Example 3 | | | 4.94 | 2c-1 | 0.06 | 1.2 |
| Comparative Example 1 | | | 5 | — | — | — |
| Comparative Example 2 | | | 4.95 | 3 | 0.05 | 1 |
| Comparative Example 3 | | | 4.95 | 4 | 0.05 | 1 |

TABLE 1-continued

| Examples | Lithium salt | Organic solvent | | Additive | | |
|---|---|---|---|---|---|---|
| | | Composition | Amount added (g) | Formula | Amount (g) | Amount added (wt %) |
| Comparative Example 4 | | | 4.95 | LiODFB | 0.05 | 1 |
| Comparative Example 5 | | | 4.95 | SN | 0.05 | 1 |

LiODFB: lithium oxalyldifluoroborate
SN: succinonitrile

EXPERIMENTAL EXAMPLES

Experimental Example 1

After the coin half-cell prepared in Example 1 and the coin half-cell prepared in Comparative Example 1 were respectively prepared in a dry room and were maintained in a 25° C. thermostat for 24 hours, a change in voltage of each coin half-cell with time was measured while performing constant current-constant voltage (CC-CV) charge and discharge at 0.1 C within a voltage range of 3.00 V to 4.25 V (vs. Li/Li$^+$). In this case, a CV current termination condition was set at 0.05 C.

Figure 1:
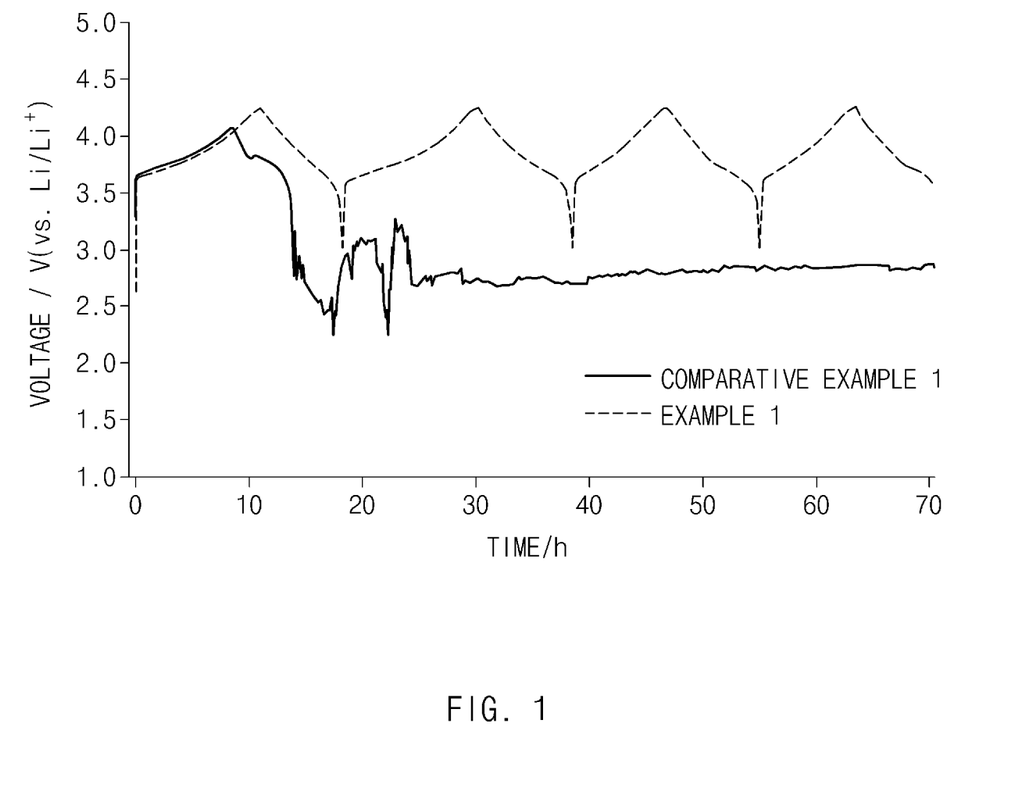
FIG. 1 is a graph illustrating changes in voltages of coin half-cells with time in Experimental Example 1 of the present invention.

As a result, as illustrated in FIG. 1, with respect to the coin half-cell of Example 1, it was normally charged and discharged, wherein a closed circuit voltage (CCV) of 4.25 V was reached during the charge and the voltage was discharged when the discharge began, but, with respect to the coin half-cell of Comparative Example 1, since the voltage did not reach 4.25 V during initial charge and an internal short-circuit occurred, it may be understood that a graph, in which the voltage dropped even when an oxidation current was applied to the positive electrode, was appeared.

That is, if the voltage of the coin half-cell increased above a potential at which iron powder may be dissolved because an oxidation reaction occurred at the positive electrode during the constant current process, iron (Fe) was dissolved from the positive electrode, and the iron (Fe) thus dissolved formed dendrites, while being electrodeposited on the surface of the Li metal as the negative electrode, to cause the internal short-circuit. As a result, with respect to the coin half-cell of Comparative Example 1, the graph, in which a charge end voltage was not reached and the potential dropped as illustrated in FIG. 1, was appeared. From these results, it may be understood that regular charge and discharge did not proceed.

In contrast, since the coin half-cell of Example 1 included the compound containing a nitrogen atom and a propargyl group as an additive in the non-aqueous electrolyte solution, the additive was adsorbed on metallic impurities to not only prevent the dissolution of the impurities, but also to prevent the formation of dendrites on the surface of the negative electrode by removing the acid formed by the decomposition of the salt, and thus, an internal short-circuit hardly occurred. Therefore, it may be understood that the graph confirmed that normal and regular charge and discharge proceeded as illustrated in FIG. 1.

Experimental Example 2

While 6 of each of the coin half-cells prepared in Examples 1 to 3 and the coin half-cells prepared in Comparative Examples 1 to 3 were charged and discharged under the same condition as in Experimental Example 1, it was confirmed whether or not an internal short-circuit of each coin half-cell occurred according to the electrolyte solution. From the results thus obtained, a degree of occurrence of the internal short-circuit (failure rate) of each of the coin half cells of Examples 1 to 3 and Comparative Examples 1 to 3 was measured, and the results thereof are then presented in Table 2 below. In this case, if an internal short-circuit occurrence rate is high in Table 2, it denotes that a low-voltage occurrence rate (failure rate) of the secondary battery is high.

TABLE 2

| | The number of coin half-cells in which internal short-circuit occurred (occurrence/preparation) | Internal short-circuit occurrence rate (%) |
|---|---|---|
| Example 1 | 2/6 | 33 |
| Example 2 | 2/6 | 33 |
| Example 3 | 2/6 | 33 |
| Comparative Example 1 | 4/6 | 67 |
| Comparative Example 2 | 3/6 | 50 |
| Comparative Example 3 | 3/6 | 50 |

As illustrated in Table 2, with respect to Comparative Example 1 in which the non-aqueous electrolyte solution not including an additive was used, it may be understood that an internal short-circuit occurrence rate was about 67% due to the decomposition product of the lithium salt and the metal dissolution of the positive electrode during charge.

In contrast, with respect to the coin half-cells of Examples 1 to 3, since the compound containing a nitrogen atom and a propargyl group was included as an additive in the non-aqueous electrolyte solution, the additive was adsorbed on the metallic impurities to not only prevent the dissolution of the impurities, but also to prevent the formation of the dendrites on the surface of the negative electrode by removing the Lewis acid formed by the decomposition of the lithium salt, and thus, it may be confirmed that internal short-circuit occurrence rates were improved by about 40% or more in comparison to that of Comparative Example 1.

With respect to the coin half-cells of Comparative Examples 2 and 3 which respectively included the non-aqueous solution including the compound of Formula 3 containing a nitrogen atom and the non-aqueous solution including the compound of Formula 4 containing a propargyl group as an additive, low-voltage occurrence rates (failure rates) were about 50%, wherein it may be confirmed that performances were relatively degraded in comparison to those of Examples 1 to 3.

Experimental Example 3. Metal (Mn) Dissolution Suppression Evaluation Test

A 20 μm thick positive electrode collector (Al foil) was coated with a mixture, in which a lithium-manganese-based active material (LiMn$_2$O$_4$) as a positive electrode active material, carbon black as a conductive agent, and polyvinylidene fluoride (PVDF), as a binder, were mixed in a ratio of 90:7.5:2.5 (wt %), dried, and roll-pressed to prepare a positive electrode.

Subsequently, the positive electrode was put in the non-aqueous electrolyte solution prepared in Example 1 and each of the non-aqueous electrolyte solutions (5 mL) prepared in Comparative Examples 1, 4, and 5 and stored at a state of charge (SOC) of 0% for 2 weeks at 60° C., and a concentration of metal (Mn) dissolved in the electrolyte solution was then measured using an inductively coupled plasma optical emission spectrophotometer (ICP-OES). An amount of the metal measured using ICP analysis is presented in FIG. 2 below.

Figure 2:
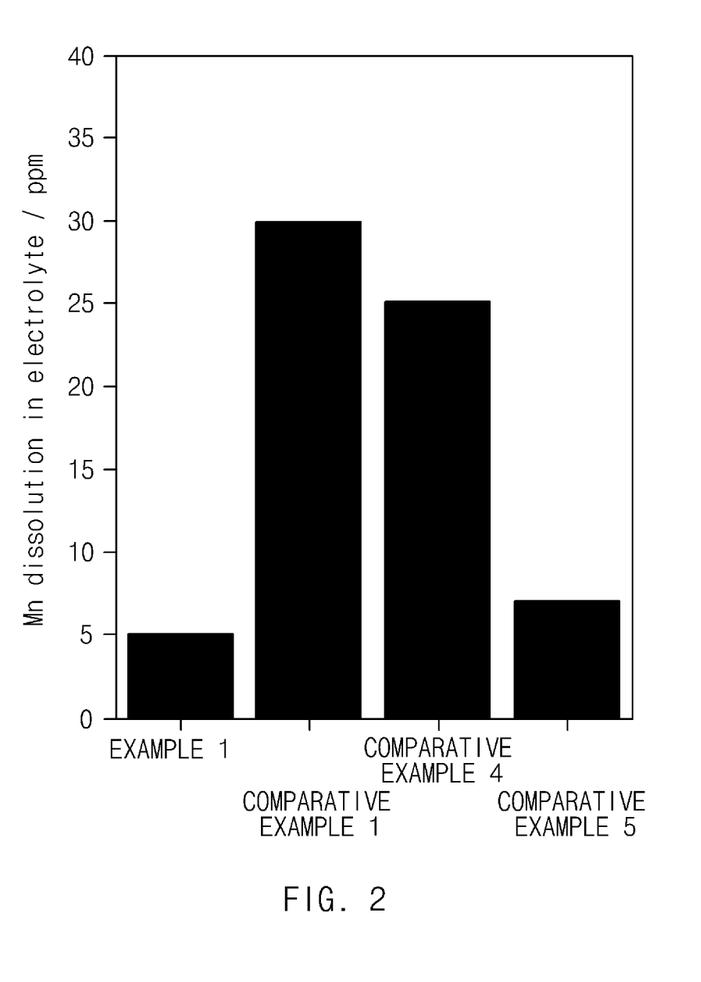
FIG. 2 is a graph illustrating metal dissolution suppression effects of non-aqueous electrolyte solutions in Experimental Example 3 of the present invention.

Referring to FIG. 2, in a case in which the non-aqueous electrolyte solution of Example 1 of the present invention was used, since the compound containing a Lewis base, which was included as the additive, may effectively remove a Lewis acid as the decomposition product of the anions of the lithium salt which was generated at high temperatures, an effect of suppressing the dissolution of the metal from the positive electrode including the lithium-manganese-based oxide was significantly improved in comparison to the cases of using the non-aqueous electrolyte solution of Comparative Example 1 without an additive, the non-aqueous electrolyte solution of Comparative Example 4 including a general electrolyte solution additive, and the non-aqueous electrolyte solution of Comparative Example 5 including a nitrile-based additive, and thus, it may be confirmed that less Mn ions were detected.

The invention claimed is:

1. A non-aqueous electrolyte solution additive comprising compound represented by Formula 1:

(Formula 1)

wherein, in Formula 1,

R1 and R2 are each independently a linear or non-linear alkyl group having 1 to 5 carbon atoms, and R$_3$ is a linear or non-linear alkylene group having 1 to 3 carbon atoms

2. The non-aqueous electrolyte solution additive of claim 1, wherein the compound represented by Formula 1 comprises at least one selected from the group consisting of compounds represented by Formulae 1a to 1c:

(Formula 1a)

(Formula 1b)

(Formula 1c)

3. A non-aqueous electrolyte solution additive comprising at least one selected from the compounds represented by Formulae 2a to 2c:

[Formula 2a]

wherein, in Formula 2a,

R$_6$ is a linear or non-linear alkylene group having 1 to 3 carbon atoms,

R$_7$ to R$_{10}$ are each independently at least one selected from the group consisting of hydrogen, an alkyl group having 1 to 3 carbon atoms, and —CN, and B is CH$_2$, O, N-CH$_3$, or wherein R' is a linear or non-linear alkylene group having 1 to 3 carbon atoms, provided that when B is CH$_2$, O, or at least one of $R_7$ to $R_{10}$ is —CN,

[Formula 2b]

wherein, in Formula 2b,
$R_{11}$ is a linear or non-linear alkylene group having 1 to 3 carbon atoms, and
$R_{12}$ to $R_{15}$ are each independently at least one selected from the group consisting of hydrogen, an alkyl group having 1 to 3 carbon atoms, and —CN, and at least one of $R_{12}$ to $R_{15}$ is —CN,

[Formula 2c]

wherein, in Formula 2c,
$R_{16}$ is a linear or non-linear alkylene group having 1 to 3 carbon atoms, and
$R_{17}$ to $R_{19}$ are each independently at least one selected from the group consisting of hydrogen, an alkyl group having 1 to 3 carbon atoms, and —CN, and
D is CH, or N.

4. The non-aqueous electrolyte solution additive of claim 3, wherein the compound represented by Formula 2a comprises at least one selected from the group consisting of compounds represented by Formulae 2a-2, 2a-3 and 2a-5:

(Formula 2a-2)

(Formula 2a-3)

(Formula 2a-5)

5. The non-aqueous electrolyte solution additive of claim 3, wherein the compound represented by Formula 2c comprises a compound represented by Formula 2c-1:

(Formula 2c-1)

6. A non-aqueous electrolyte solution for a lithium secondary battery, the non-aqueous electrolyte solution comprising:
a lithium salt;
an organic solvent; and
a non-aqueous electrolyte solution additive comprising at least one compound selected from the group consisting of compounds represented by Formulae 1 and 2:

(Formula 1)

wherein, in Formula 1,
R1 and R2 are each independently a linear or non-linear alkyl group having 1 to 5 carbon atoms, and $R_3$ is a linear or non-linear alkylene group having 1 to 3 carbon atoms, and (Formula 2)

wherein, in Formula 2,
$R_4$ is a linear or non-linear alkylene group having 1 to 3 carbon atoms,
A is a substituted or unsubstituted nitrogen-containing heteroaryl group having 3 to 6 carbon atoms, a substituted or unsubstituted nitrogen-containing heteroaryl group having 3 to 6 carbon atoms which includes at least one of oxygen and nitrogen elements, a substituted or unsubstituted nitrogen-containing heterocyclic group having 3 to 6 carbon atoms, or a substituted or unsubstituted nitrogen-containing heterocyclic group having 3 to 6 carbon atoms which includes at least one of oxygen and nitrogen elements,
$R_5$ is at least one selected from the group consisting of hydrogen, an alkyl group having 1 to 3 carbon atoms, —CN, and wherein R is a linear or non-linear alkylene group having 1 to 3 carbon atoms,
n is an integer of 1 to 6, and
when n is 2 or more, $R_5$'s are the same or different from each other.

7. The non-aqueous electrolyte solution for a lithium secondary battery of claim 6, wherein the non-aqueous electrolyte solution additive is included in an amount of 0.05 wt % to 5 wt % based on a total amount of the non-aqueous electrolyte solution.

8. The non-aqueous electrolyte solution for a lithium secondary battery of claim 7, wherein the non-aqueous electrolyte solution additive is included in an amount of 0.5 wt % to 3 wt % based on the total amount of the non-aqueous electrolyte solution.

9. A lithium secondary battery comprising a negative electrode, a positive electrode, a separator disposed between the negative electrode and the positive electrode, and a non-aqueous electrolyte solution,
wherein the positive electrode comprises a positive electrode active material selected from the group consisting of a lithium-nickel-manganese-cobalt-based oxide and a lithium-manganese-based oxide, and
the non-aqueous electrolyte solution is the non-aqueous electrolyte solution for a lithium secondary battery of claim 6.

10. The lithium secondary battery of claim 9, wherein the positive electrode active material comprises a lithium-manganese-based oxide.

11. The lithium secondary battery of claim 10, wherein the lithium-manganese-based oxide is $LiMn_2O_4$.

12. The non-aqueous electrolyte solution for a lithium secondary battery of claim 6, wherein the lithium salt comprises $Li^+$ as a cation, and at least one selected from the group consisting of $F^-$, $Cl^-$, $Br^-$, $I^-$, $NO_3^-$, $N(CN)_2^-$, $BF_4^-$, $ClO_4^-$, $PF_6^-$, $(CF_3)_2PF_4^-$, $(CF_3)_3PF_3^-$, $(CF_3)_4PF_2^-$, $(CF_3)_5PF^-$, $(CF_3)_6P^-$, $F_3SO_3^-$, $CF_3CF_2SO_3^-$, $(CF_3SO_2)_2N^-$, $(FSO_2)_2N^-$, $CF_3CF_2(CF_3)_2CO^-$, $(CF_3SO_2)_2CH^-$, $(SF_5)_3C^-$, $(CF_3SO_2)_3C^-$, $CF_3(CF_2)_7SO_3^-$, $CF_3CO_2^-$, $CH_3CO_2^-$, $SCN^-$, and $(CF_3CF_2SO_2)_2N^-$ as an anion.

13. The non-aqueous electrolyte solution for a lithium secondary battery of claim 6, wherein the organic solvent comprises at least one selected from the group consisting of an ether-based solvent, an ester-based solvent and an amide-based solvent.

14. The non-aqueous electrolyte solution for a lithium secondary battery of claim 6, wherein the organic solvent comprises at least one selected from the group consisting of a cyclic carbonate compound, a linear carbonate compound, a linear ester compound, and a cyclic ester compound.

15. The non-aqueous electrolyte solution for a lithium secondary battery of claim 6, further comprising at least one additive selected from the group consisting of a silicon-based compound including a vinyl group, vinylene carbonate, vinyl ethylene carbonate, fluoroethylene carbonate, cyclic sulfite, saturated sultone, unsaturated sultone, and a non-cyclic sulfone.

16. The lithium secondary battery of claim 9, wherein the positive electrode active material further comprises at least one lithium transition metal oxide selected from the group consisting of lithium-cobalt-based oxide, lithium-nickel-based oxide, lithium-nickel-manganese-based oxide, lithium-nickel-cobalt-based oxide, lithium-manganese-cobalt-based oxide, and lithium-nickel-cobalt-transition metal oxide.

* * * * *